US005620436A

United States Patent [19]
Lang et al.

[11] Patent Number: 5,620,436
[45] Date of Patent: Apr. 15, 1997

[54] METHOD AND APPARATUS FOR PROVIDING PRECISE LOCATION OF POINTS ON THE EYE

[75] Inventors: Stefan Lang, Munich, Germany; David R. Clonts, Houston, Tex.

[73] Assignee: Chiron Technolas GmbH Ophthalmologische Systeme, Germany

[21] Appl. No.: 672,307

[22] Filed: Jun. 28, 1996

Related U.S. Application Data

[63] Continuation of Ser. No. 310,656, Sep. 22, 1994, abandoned.

[51] Int. Cl.$^6$ .............................. A61B 17/36; A61N 5/02
[52] U.S. Cl. .................................................. 606/4; 606/12
[58] Field of Search ...................... 606/4, 5, 6, 10, 606/11, 12

[56] References Cited

U.S. PATENT DOCUMENTS

| | | | |
|---|---|---|---|
| 4,443,075 | 4/1984 | Crane | 606/4 |
| 4,665,913 | 5/1987 | L'Esperance, Jr. . | |
| 4,669,466 | 6/1987 | L'Esperance . | |
| 4,695,163 | 9/1987 | Schachar | 356/369 |
| 4,718,418 | 1/1988 | L'Esperance, Jr. . | |
| 4,729,372 | 3/1988 | L'Esperance, Jr. . | |
| 4,732,148 | 3/1988 | L'Esperance, Jr. . | |
| 4,770,172 | 9/1988 | L'Esperance, Jr. . | |
| 4,773,414 | 9/1988 | L'Esperance, Jr. . | |
| 4,784,135 | 11/1988 | Blum et al. . | |
| 4,788,975 | 12/1988 | Shturman et al. . | |
| 4,798,204 | 1/1989 | L'Esperance, Jr. . | |
| 4,848,340 | 7/1989 | Bille et al. | 606/5 |
| 4,901,718 | 2/1990 | Bille et al. | 606/4 |

(List continued on next page.)

FOREIGN PATENT DOCUMENTS

| | | |
|---|---|---|
| 1059654 | 7/1979 | Canada . |
| 111060 | 9/1983 | European Pat. Off. . |
| 151869 | 11/1984 | European Pat. Off. . |
| 164858 | 4/1985 | European Pat. Off. . |
| 191688 | 1/1986 | European Pat. Off. . |
| 207648 | 6/1986 | European Pat. Off. . |
| 224322 | 9/1986 | European Pat. Off. . |
| 257836 | 7/1987 | European Pat. Off. . |
| 280414 | 1/1988 | European Pat. Off. . |
| 306409 | 1/1988 | European Pat. Off. . |
| 296982 | 6/1988 | European Pat. Off. . |
| 299836 | 6/1988 | European Pat. Off. . |
| 326760 | 12/1988 | European Pat. Off. . |
| 356282 | 7/1989 | European Pat. Off. . |
| 400471 | 5/1990 | European Pat. Off. . |

(List continued on next page.)

OTHER PUBLICATIONS

"A new method of analyzing vectors for changes in astigmatism", Noel Alpins Journal of Cataract Refractive Surgery vol. 19 Jul. 1993 pp. 524–533.

Thompson, Frank B. and McDonnell, Peter J., "Color Atlas/Text of Excimer Laser Surgery: The Cornea", 1993 Igaku–Shoin Medical Publishers, Inc., pp. 30–33; 41; 53–62; 77–92.

Photonics Spectra, Annual European Issue, Special Report: Photonics Adjusts to the Shifting Ground of the New Europe, Jun. 1993.

Hower, Wendy "ISCAN Sees the Future Through Your Own Eies," Boston Business Journal, vol. 11, No. 24, © 1991 P&L Publications Inc. (Aug. 5, 1991) p. 4.

Trokel, et al., "Excimer Laser Surgery of the Cornea," Am. J. Ophthalmology 96:710–715, 1983.

*Primary Examiner*—Angela D. Sykes
*Assistant Examiner*—Sonya Harris-Ogugua
*Attorney, Agent, or Firm*—Pravel, Hewitt, Kimball & Krieger

[57] ABSTRACT

A method and apparatus for providing more precise aiming by an eye tracking system, including a registration, or aiming, laser, that provides for precise location of where the next laser ablation shot will impinge upon the eye. The method and apparatus further includes an aiming assistance fixture that provides a fixed frame of reference for locating the origin of the eye.

13 Claims, 5 Drawing Sheets

U.S. PATENT DOCUMENTS

| | | | |
|---|---|---|---|
| 4,941,093 | 7/1990 | Marshall et al. | 364/413.01 |
| 4,973,330 | 11/1990 | Azema et al. | 606/5 |
| 5,037,207 | 8/1991 | Tomel et al. | 356/444 |
| 5,054,907 | 10/1991 | Sklar et al. | 351/212 |
| 5,098,426 | 3/1992 | Sklar et al. | 606/5 |
| 5,108,388 | 4/1992 | Trokel | 606/5 |
| 5,162,641 | 11/1992 | Fountain | 250/201 |
| 5,284,477 | 2/1994 | Hanna et al. | 606/5 |
| 5,350,374 | 9/1994 | Smith | 606/5 |
| 5,391,165 | 2/1995 | Fountain et al. | 606/4 |
| 5,439,462 | 8/1995 | Bille et al. | 606/6 |
| 5,445,633 | 8/1995 | Nakamura et al. | 606/5 |
| 5,490,849 | 2/1996 | Smith | 606/5 |

FOREIGN PATENT DOCUMENTS

| | | |
|---|---|---|
| 412789 | 8/1990 | European Pat. Off. . |
| 391376 | 10/1990 | European Pat. Off. . |
| 447067 | 2/1991 | European Pat. Off. . |
| 3532464 | 9/1985 | Germany . |
| 3800076 | 1/1988 | Germany . |
| 4001434 | 8/1990 | Germany . |
| WO86/02730 | 5/1986 | WIPO . |
| WO90/11054 | 10/1990 | WIPO . |
| WO91/19539 | 12/1991 | WIPO . |
| WO92/01430 | 2/1992 | WIPO . |
| WO92/03186 | 3/1992 | WIPO . |
| WO92/03187 | 3/1992 | WIPO . |
| WO93/08877 | 5/1993 | WIPO . |

METHOD AND APPARATUS FOR PROVIDING PRECISE LOCATION OF POINTS ON THE EYE

This is a continuation of application Ser. No. 08/310,656, filed on Sep. 22, 1994 now abandoned.

BACKGROUND OF THE INVENTION

1. Field of the Invention

The invention relates to improvements to optical aiming systems used in conjunction with excimer laser eye surgery systems, and more specifically, to a method and apparatus for improving the effectiveness of such an optical aiming system in locating points on the eye.

2. Description of the Related Art

The advent of the excimer laser opened a whole new realm of possibilities for eye surgery, providing a non-invasive technique for resculpting the surface of the eye itself to match a desired curvature. Such systems are well known in the art, and are further described, for example, in the inventor's PCT Application PCT/EP93/02667 which is hereby incorporated by reference, as well as in various patents to L'Esperance, such as U.S. Pat. No. 4,665,913.

To improve the accuracy of these excimer laser surgical devices, it is preferable to precisely place each shot from the excimer laser at the desired location. A number of techniques and devices have been developed to achieve this end. For example, a simple fixation light has often been used. Patients fixate their gaze upon that light, generally lessening slow eye movement. This technique does not, however, prevent rapid movements of the eye. Further, a momentary lapse in fixation could result in an ablation shot far from the intended shot location. As an alternative, physical fixation devices have been used which immobilize the eye by physically connecting to the eye, thereby holding it steady.

A more recent technique involves the use of computer aided eye tracking devices. These are optical or topographic location systems that typically use a video camera to either optically or topographically locate and track the center of the eye. Each shot can then be placed at any desired location on the eye relative to that center. Examples of such systems can be found in U.S. Pat. No. 5,098,426 to Sklar et al., U.S. Pat. No. 5,162,641 to Fountain, and U.S. Pat. No. 4,848,340 to Bille. These systems use various techniques to track the center of the eye, such as a computer mapped digital image from a video camera. For example, U.S. Pat. No. 5,098,426, to Sklar, et al., hereby incorporated by reference, describes an eye tracking system that generates a three dimensional profile of the eye and tracks movement by noting changes in that profile. The Sklar patent shows an eye tracker using a slow control loop and a fast control loop. The slow control loop relies on a video camera to provide topographical information that the eye tracker then uses to aim the system optics.

An alternative eye tracking system is shown in U.S. Pat. No. 4,848,340 to Bille, also incorporated by reference. The Bille patent shows a strictly optical, rather than topographical, based system that tracks a reference grid which has been ablated into the eye.

Another eye tracking system using infrared light to illuminate the pupil of the eye has been announced by ISCAN, Inc. This system is described as using infrared light to illuminate the eye, with the system then returning positioning information to a variety of applications, such as computer control through eye movement and assistance to the disabled.

Any of a various number of techniques for locating objects can be readily adapted to locate the center of the eye. It would be desirable, however, to improve the effectiveness and accuracy of such systems. That is, given an object location system used in conjunction with an excimer laser system, it would be desirable to provide other improvements that enhance the ability of those systems to accurately locate the center of the eye and provide for accurate aiming of the pulsed excimer beam onto the eye.

These eye tracking systems are not without problems, however. First, misalignment of the optics can result in offsets of where each excimer laser shot actually falls relative to where it should fall. For example, servomotors can be slightly miscalibrated, resulting in these offsets. It would thus be desirable to provide a method and apparatus for eliminating the effects of such miscalibrations.

Second, these systems tend to be either invasive or complicated, in the sense that they require actual physical markings to be made on the eye, as shown in the Bille patent, or require highly complex topographical location systems and multiple feedback loops for locating the center of the eye, as shown in Sklar patent. Thus, simpler methods of providing a reference to the center of the eye would be desirable.

SUMMARY OF THE INVENTION

In accordance with the invention, an aiming fixture is provided for an eye tracking system so that the eye tracking system can achieve more accurate registration of the location of the eye. In variations according to the invention, the aiming fixture is provided as a triangle, hexagon, or other regular object. Further, the fixation ring is preferably constructed to provide registration at one point to determine rotation of the fixation ring.

Further according to the invention, a registration laser is provided along the optical path of the pulsed excimer beam, allowing an eye tracking system to accurately determine where the next excimer laser shot will fall on the surface of the eye.

BRIEF DESCRIPTION OF THE DRAWINGS

A better understanding of the present invention can be obtained when the following detailed description of the preferred embodiment is considered in conjunction with the following drawings, in which.

DETAILED DESCRIPTION OF THE PREFERRED EMBODIMENT

Figure 1:
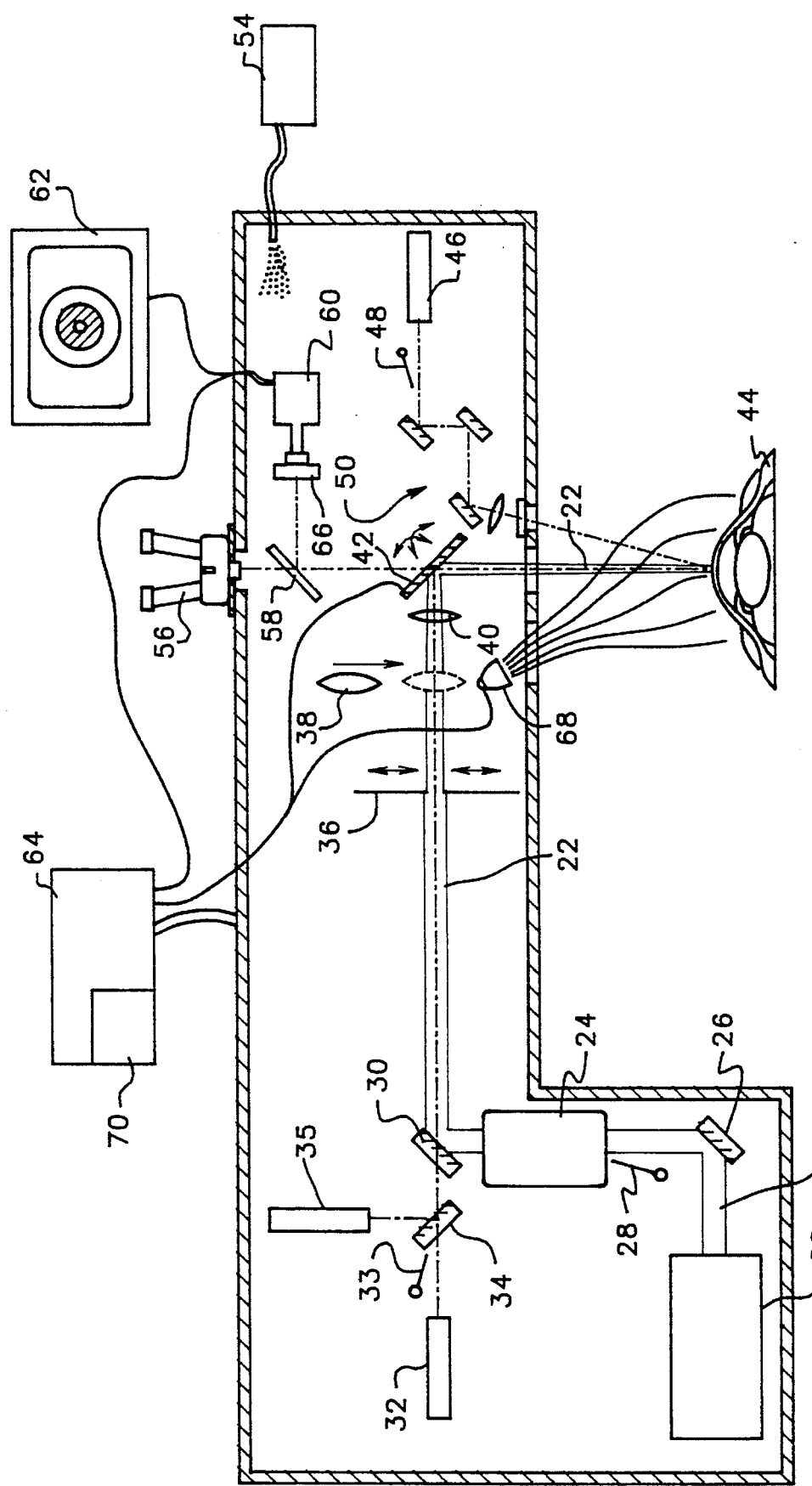
FIG. 1 is a diagram illustrating a typical excimer laser eye surgery system in which can be implemented the apparatus and method according to the invention.

Turning now to the drawings, FIG. 1 shows the typical eye surgery system 10 in and with which the method and apparatus according to the invention would be implemented. An excimer laser 20 provides a pulsed beam 22 to a beam homogenizer 24 after reflection from optics 26. A shutter 28 is also provided to block transmission of the pulsed beam 22 to the beam homogenizer 24. The excimer laser 20 is a typical excimer laser as is well known in the art. It preferably provides a 193 nm wavelength beam with a maximum pulse energy of 400 mJ/pulse. The excimer laser 20 preferably provides maximum average power at the treatment site of 1 W, with a pulse frequency of 10 Hz and a pulse length of 18 ns. Of course a variety of other excimer lasers could be used, and the apparatus and method according to the invention further have application where a laser other than an excimer laser is used. By way of example, the wavelength of the light from the laser is preferably less than 400 nm, as that provides the desired ablating action with reduced thermal heating. Further, other pulse energies can be provided, such as all the way down to 200 mJ/pulse, with typical repetition rates of 60 to 100 pulses per second with a typical pulse length of 10 to 30 ns. Again, all of these are merely typical values, and deviation from them can be made without changing the spirit of the apparatus and method according to the invention. Further examples of such laser systems can be found in U.S. Pat. No. 4,665,913, entitled "Method for ophthalmological Surgery," issued May 19, 1987, and U.S. Pat. No. 4,729,372, entitled "Apparatus for Performing ophthalmic Laser Surgery," issued Mar. 8, 1988.

The beam homogenizer 24 preferably includes standard homogenization and focusing hardware, which can be based both on optical mixing of the beam and on rotation of the beam. For an example of typical beam homogenization hardware, see U.S. Pat. No. 4,911,711 entitled, "Sculpture Apparatus for Correcting Curvature of the Cornea," issued Mar. 27, 1990. From the beam homogenizer 24, the pulsed beam 22 is then reflected off of optics 30, which also passes an aiming beam from an aiming laser 32. This aiming laser 32 is preferably a red 633 nm helium neon laser of less than 1 mW/cm$^2$ of power. The aiming beam from the aiming laser 32 can also be blocked by a shutter 33. The aiming laser 32 is aligned so that its optical pathway coincides with the pulsed beam 22. The aiming laser 32 provides an aiming beam spot that coincides with the central axis of the laser shot of the pulsed beam 22.

A registration laser 35 also provides a registration beam reflected by optics 34. The registration laser 35 preferably is of a wavelength of approximately 950 nm, or near infrared, and preferably is low power, less than 1 mW/cm$^2$.

The size of the registration beam from the registration laser 35 is preferably small, less than 0.5 mm in diameter. This registration beam provides for precise aiming of the pulsed beam 22, as is discussed below in conjunction with the discussion of FIGS. 2 and 3.

Although the separate aiming laser 32 and registration laser 35 are disclosed, these could be combined to provide a single aiming/registration beam depending on subsequent optics in the system. The aiming beam from the aiming laser 32 and the registration beam from the registration laser 35 are preferably both coaxially aligned with the pulse beam 22.

In the disclosed embodiment, the registration laser 35 and the aiming laser 32 are separate because, as discussed below, while the aiming laser 32 provides a spot of visible light to the surgeon, that light is filtered out by the imaging system. Surgeons need to directly observe the eye 44 during manual surgery, for example, such as when they manually perform theraputic surgery or when they manually designate the location of the center of the eye. Then, the visible light is necessary. With an alternative embodiment in which the imaging system does not remove the visible light, for example, the aiming laser 32 and the registration laser 35 could be one and the same.

From the optics 30, the pulsed beam 22 (now also co-aligned with the aiming beam from the aiming laser 32 and the registration beam from the registration laser 35) then passes through an adjustable diaphragm 36, which allows the beam size of the pulsed beam 22 to be adjusted before it enters the final optics.

Following the adjustable diaphragm 36, a focusing lens 40 directs the pulsed beam 22 onto a scanning mirror 42, which then reflects the beam 22 onto a patient's eye 44. The scanning mirror is preferably capable of moving a beam at 5000 mm/sec at the surface of the eye 44. The focusing lens 40 focuses light such that when the eye 44 is at the optimal distance, the pulsed beam 22 is properly focused onto the eye 44.

These various lenses and mirrors thus combine to form an optical system providing an excimer beam to the cornea. The optical system creates a laser spot on the cornea, and the spot size is adjustable, along with its location. It will be readily appreciated that a wide variety of different systems could be used to optically provide such a beam. For example, a lens could be used to adjust the spot size rather than an aperture, and instead of a scanning mirror, the patient or the patient's eye 44 could be physically moved to provide for shots at different locations on the eye 44.

Also provided in the system according to the invention is a focusing laser 46, whose beam can also be blocked by a shutter 48. The focusing laser 46 is preferably a green helium neon laser providing a beam of a wavelength of 535 nm and less than 1 mW of power. The beam from the focusing laser 46 travels through optics 50 and impinges on the eye 44 at an angle. The distance of the eye 44 from the eye surgery system 10 is adjusted such that both the beam from the aiming laser 32 and the beam from the focusing laser 46 impinge on the surface of the eye 44 at the same point.

A clean gas purge unit 54 ensures that the optics and the beams in the system are free from any floating debris.

A microscope 56 is provided for the physician to observe progress during ablation of the surface of the eye 44. The microscope 56 is preferably a ZEISS OPMI "PLUS" part No. 3033119910, with magnifications of 3.4, 5.6 and 9.0 times. Field illumination is provided by a cold light source not shown, which is preferably the Schott KL1500 Electronic, ZEISS part number 417075. This microscope 56 focuses through the scanning mirror 42 and also focuses through a splitting mirror 58. The splitting mirror further provides a view of the eye 44 to a video camera 60. The video camera 60 is preferably sensitive to both visible and infrared light, and is preferably a high resolution S-VHS camera with 400,000 pixels, and generating 50 frames per second, although it could be any of a variety of other cameras or detection grids, including an NTSC camera with a 60 frame per second rate. The video camera 60 preferably provides an image output to a capturing video screen 62 and to a control unit 64. The video camera 60 is preferably capable of producing digitized output to provide to the control unit 64.

Preferably filtering light into the video camera 60 is an infrared filter 66, which only permits infrared light to pass through. This would permit for example, a spot created by the registration beam from the registration laser 35 to be perceived by the video camera 60. Thus, the video camera 60 and infrared filter 66 combine to form an infrared sensitive video unit.

In addition to visible light, the eye 44 is also illuminated by an infrared light source 68. The infrared light source 68 is preferably a 880 nm diffuse light source from a 10 LED array, but could be any of a number of other known sources, such as a halogen lamp with an appropriate filter. The infrared light source 68 is preferably of lower intensity than the registration beam from the registration laser 35, and in any case less than 1 mW/cm$^2$. The infrared light source 68 is preferably controlled by the control unit 64 and provides either a fixed or adjustable degree of illumination of infrared light onto the eye 44. It will be appreciated that the image of the eye 44 illuminated by the infrared light source 68 is also perceptible by the video camera 60 through the infrared filter 66.

It has been found that use of the infrared light source 68 in conjunction with the infrared filter 66 improves the contrast of the features of the eye 44, no matter what intensity of visible light is cast on the eye 44. The control unit 64 can then control the infrared light source 68 to provide the desired contrast at the video camera 60. In this way, the aiming function of the control unit 64 and the movable mirror 42 are unaffected by changes in visible light onto the eye 44. For example, if the surgeon needs more illumination, he can adjust an visible light source, while the infrared light source 68 remains being controlled by the control unit 64. By providing the infrared light source 68, contrast is thus improved, and the performance of an eye tracker used in conjunction with the eye surgery system 10 is thus improved. This improved contrast is even apparent when the infrared filter 66 is omitted.

The control unit 64, which is typically a high performance computer compatible with an IBM PC by International Business Machines Corp., preferably controls all components of the eye surgery system 10, including the shutters 28, 34, and 48, the diaphragm 36, the spot mode lens 38, and the scanning mirror 42, and the infrared light source 68. Ablation profiles software runs on the control unit 64, such as the ablation software described in the inventor's PCT application PCT/EP93/02667. The various types of ablation software known to the art would all benefit from the improved aiming and registration provided by the invention.

The control unit also preferably contains an eye tracking system 70. In one embodiment, the eye tracking system 70 may be a proprietary software system developed for Chiron Vision/Technolas, which runs on one Transputer™ manufactured by INMOS Limited used in conjunction with a Transputer Frame Grabber™ manufactured by Parsytech, GmbH. The eye tracking system 70 preferably receives the digitized output from the video camera 60 and then provides coordinates of the center of the eye on that video image relative to a preset origin. Further, the eye tracking system 70 should provide the coordinates of an infrared spot on the eye 44 created by the registration laser 35. These coordinates are then used by the ablation profile software in the control unit 64 to aim the scanning mirror 42 for the next shot from the excimer laser 20.

Other eye tracking systems which can be utilized with similar effect in alternate embodiments are known to the art and include those described in the Sklar and Bille patents discussed above, as well as the devices marketed by ISCAN.

Figure 2:
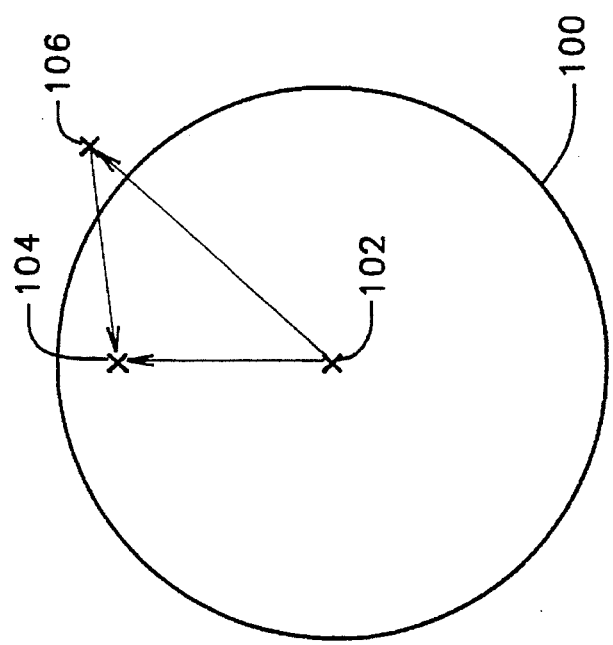
FIG. 2 is a diagram illustrating how a registration beaming from an aiming laser spot according to the invention can be used to precisely position the excimer laser system for the next pulsed excimer shot.

FIG. 2 is a diagram illustrating how the registration beam from the registration laser 35 provides for precise aiming when used in conjunction with the eye tracking system 70 and the control unit 64. The eye 44 contains, for example, a treatment area 100 within which will be created a typical laser ablation profile. The generation of such profiles is well known in the art, and can require both on-axis and off-axis ablation. Further, such treatments can use both large and small beam sizes from the pulsed laser 20.

The eye tracking system 70 provides the coordinates of a central point, or origin 102, relative to the treatment area 100, based on whatever method of operation the eye tracking system 70 uses. For example, if an eye tracking system according to the Bille patent were used, reference marks not shown would be used to locate the origin 102. Similarly, if an eye tracking system according to the Sklar patent were used, the origin 102 would be located using topographical data developed according to that system.

The ablation profile software running in the control unit 64 calculates the coordinates relative to the origin 102 of a desired target point 104, which denotes the center of the next desired excimer pulse on the eye 44 from the excimer laser 20. Having received the absolute coordinates of where the origin 102 is located on the video image from the eye tracking system 70, the ablation profile software then knows the absolute coordinates of the target point 104.

Then, the image from the video camera 60 allows the eye tracking system 70 to locate and provide the absolute coordinates of a registration spot 106 where the registration beam from the registration laser 35 impinges on the eye 44. This registration spot 106 denotes the center point of where the next pulse from the excimer laser 20 would impinge on the eye if a shot were immediately fired. In FIG. 2, this point is not in alignment with the desired target point 104, perhaps because of intervening movement of the eye 44. As discussed below in conjunction with FIG. 3, the aim of the pulsed beam 22 is therefore corrected such that the registration spot 106 coincides with the target point 104. This alignment is then again checked, and when within acceptable limits, the excimer laser 20 is fired.

An advantage of this technique is the fact that the registration beam from the registration laser 35 is aligned with the pulsed beam 22 from the pulsed excimer laser 20. If the movable mirror 42 becomes uncalibrated, this does not matter, because one always knows where the next shot from the excimer laser 20 will actually fall.

Further, misalignment of the video camera 60 along the optical axis is similarly of no consequence, as the control unit 64, using the video camera 60, can always determine where the next shot from the pulsed excimer laser 20 will strike relative to the origin 102.

Further, slight misalignment of the registration laser 35 is similarly of no consequence, as that misalignment will result in a fixed offset from the center of the pulsed beam 22. Simple calibration software can determine this offset, and then correct for this offset in determining where the center of the next shot from the excimer laser 20 will fall relative to the registration spot 106.

It will be appreciated that the registration laser 35 and the aiming laser 32 can be combined if the infrared filter 66 is omitted. Then, the registration spot 106 would be created by those combined lasers, and would be visible to the video camera 60 whether that combined laser produced an infrared spot or a visible spot. In that case, the combined laser would preferably create a visible spot so as to be observable by the surgeon through the microscope 56.

Figure 3:
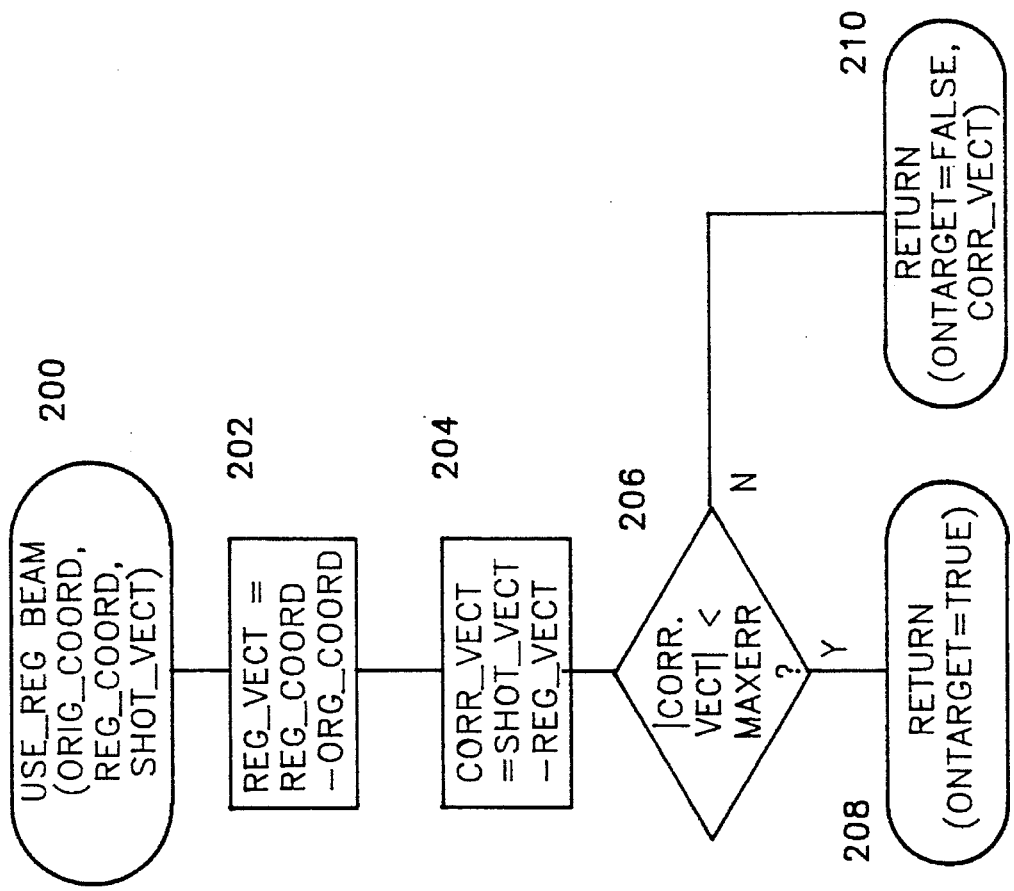
FIG. 3 is a flowchart illustrating how software can be used in conjunction with an eye tracking system and an ablation profile system to more precisely aim the excimer laser using the registration spot illustrated in FIG. 2.

FIG. 3 is a flowchart illustrating a use registration beam routine USE_REGBEAM 200 to be used by the ablation profile software in the control unit 64 to implement the aiming function of the registration laser 35. The ablation profile software would call the USE_REGBEAM routine 200 before each shot is fired from the excimer laser 20. The USE_REGBEAM routine 200 preferably receives three parameters from the ablation profile software. First, a parameter ORIG_COORD contains the absolute coordinates of the origin 102 in the digitized video image. This was of course located by the ablation profile software for the eye tracking system 70. Second, a parameter REG_COORD contains the absolute coordinates of the center of the registration spot 106 in the digitized video image, again as located by the eye tracking system 70. Finally, a parameter SHOT_VECT contains the coordinates of the target point 104 relative to the origin 102. This is calculated by the ablation profile software.

Note that while the origin 102 is preferably the visual axis of the eye, it could be set to any other arbitrary "origin" needed by the ablation profile software. The eye tracking system 70 will previously have assigned that desired point as the origin 102 and will always be able to relocate that origin 102. After all, this is what the eye tracking system 70 does. It would be set, for example, manually by the doctor before beginning a course of treatment, and the eye tracking system 70 would then "lock on" to that particular origin 102.

Proceeding to step 202, the USE_REGBEAM routine 200 sets a registration vector REG_VECT equal to the offset of the registration spot 106 from the origin 102. This is done by normalizing REG_COORD. That is, ORIG_VECT is subtracted from REG_COORD giving REG_VECT, which then is the position of the registration spot 106 relative to the origin 102, rather than the absolute position of the registration spot 106. This is stored as a vector offset from the origin 102.

Note that SHOT_VECT is already normalized, as the ablation profile software will have provided the coordinates of the target point 104 relative to the origin 102.

Proceeding to step 204, the USE_REGBEAM routine 200 sets a correction vector CORR_VECT equal to SHOT_VECT minus REG_VECT. CORR_VECT corresponds to the amount the aim of the excimer laser must be adjusted, here by the scanning mirror 42, to bring the registration spot 106 in line with the desired target point 104.

Proceeding to step 206, the USE_REGBEAM routine 200 determines the magnitude of CORR_VECT and whether it is less than MAXERR, which is either a constant or variable. MAXERR would be the maximum allowed offset from the desired target spot 104 at which the system will allow an excimer laser shot to be fired. For example, MAXERR could be set to 10% of the radius of the next excimer laser shot as determined by the ablation profile software, or could be set to an arbitrary magnitude such as 50 microns.

If at step 206 it is determined that CORR_VECT is less than MAXERR, the USE_REGBEAM routine 200 proceeds to step 208, where it returns to the ablation profile software with a variable ONTARGET set true. This tells the ablation profile software that the registration spot 106 is appropriately aligned with the target point 104. The ablation profile software would then fire the excimer laser 20 and proceed to processing the next desired target point.

If at step 206 it was determined that the magnitude of CORR_VECT is not less than MAXERR, however, indicates the registration spot 106 is not appropriately aligned with the target point 104. In that case, the USE_REGBEAM routine 200 proceeds to step 210, where it returns to the ablation profile software with ONTARGET set false, and also returns CORR_VECT to the ablation profile software. The ablation profile software would then preferably reaim the system using the scanning mirror 42 and the value of CORR_VECT and again call the USE_REGBEAM routine 200. It would preferably repeat these steps until ONTARGET was returned true, indicating that it would be appropriate to fire the next shot from the excimer laser 20. The ablation profile software, in re-aiming the scanning mirror 42, moves that scanning mirror 42 by an amount necessary to move the registration spot 106 by an amount corresponding to CORR_VECT.

By using the USE_REGBEAM routine 200 in conjunction with the registration laser 35 and the eye tracking system 70, the ablation profile software can accurately position the pulsed beam 22 for the firing of the next shot. As noted above, the USE_REGBEAM routine 200 is unaffected by lack of calibration of the scanning mirror 42, as long as the scanning mirror 42 responds somewhat predictably. The responsiveness of the aiming mirror can be determined initially through calibration routines, such as by seeing how much the registration spot 106 moves in response to an arbitrary adjustment of the calibration mirror. This responsiveness could even be determined to be different in more than one direction.

Similarly, if the beam from the registration laser 35 and the pulsed beam 22 are slightly out of line, that predetermined offset can be added to REG_VECT at step 202. Because that offset would be constant, it would not affect the USE_REGBEAM routine 200.

Figure 4A:
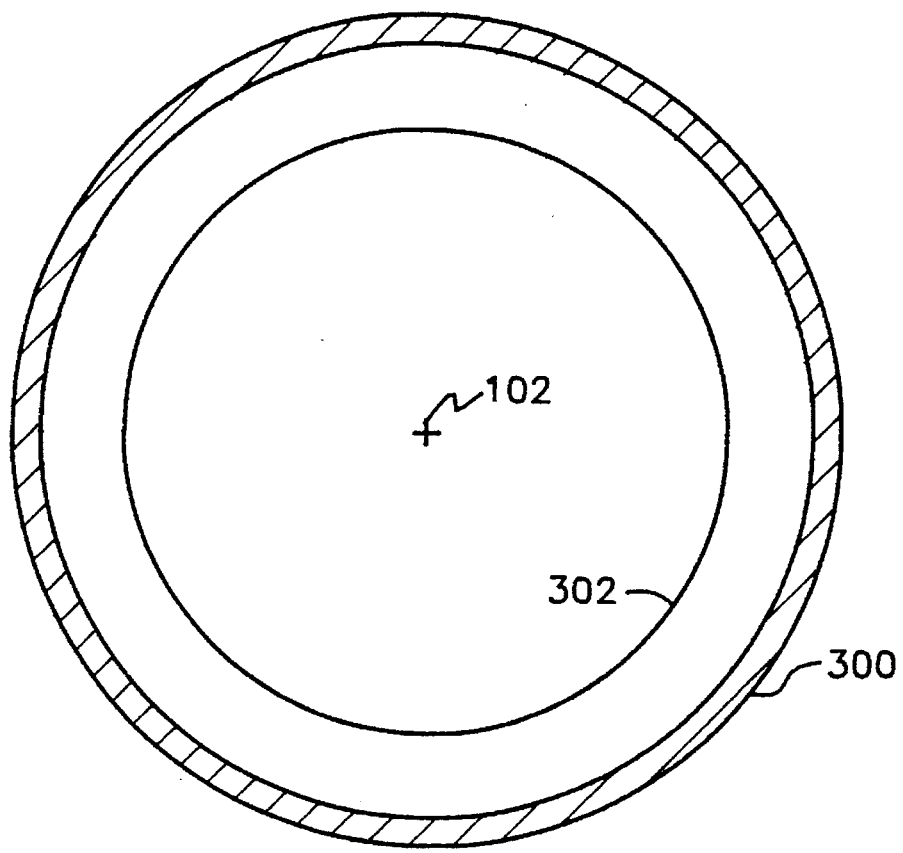
FIGS. 4A and 4B are top and side views of an aiming fixture according to the invention to improve performance of an eye tracking system.
Figure 4B:
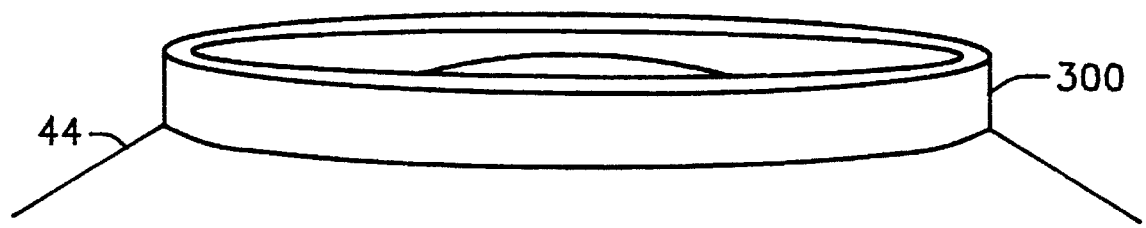
Figure 5A:
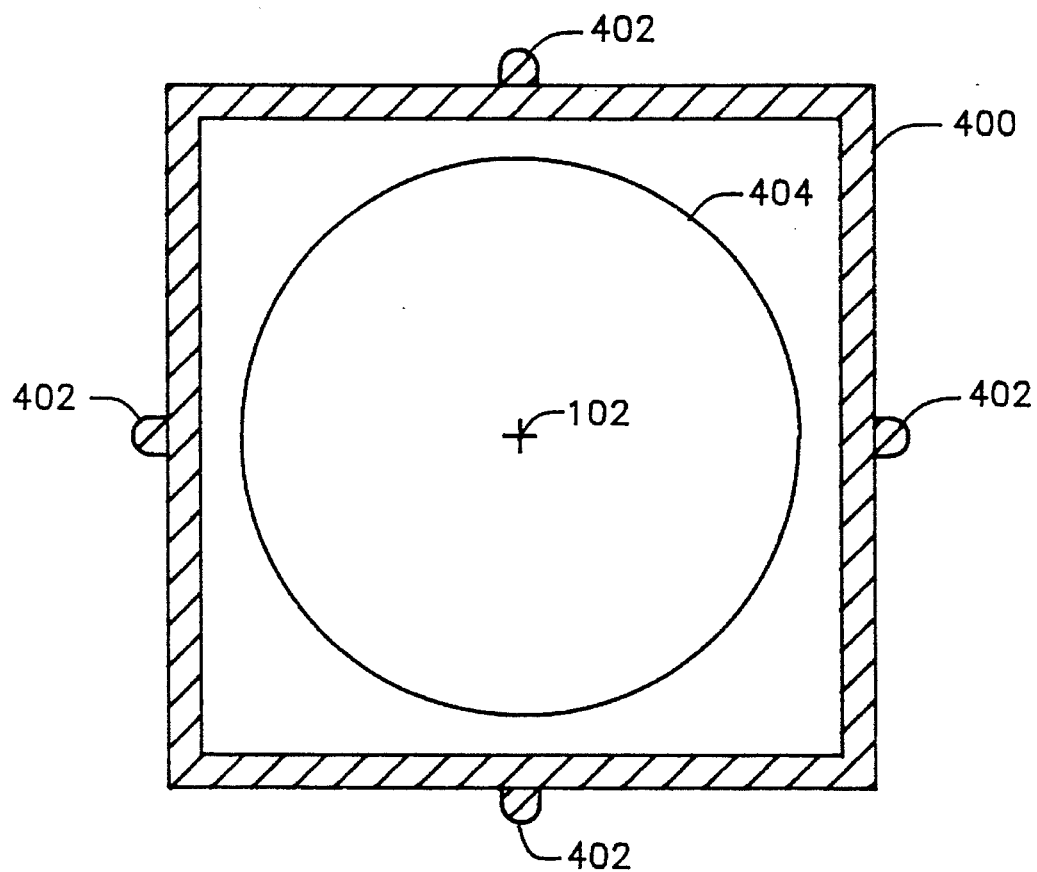
FIGS. 5A and 5B are top and side views of an alternative embodiment of the aiming fixture of FIGS. 4A and 4B.
Figure 5B:
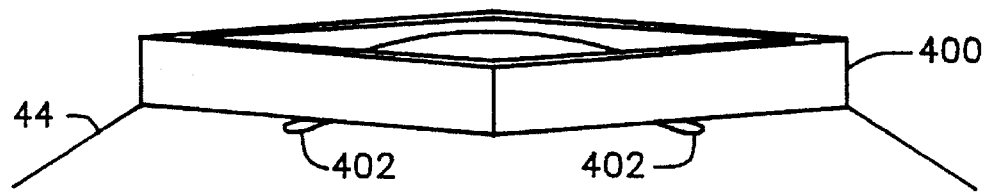

FIGS. 4A and 4B show a circular aiming assistance fixture 300 according to the invention. FIG. 4A is a top view, while FIG. 4B is a side view. FIGS. 5A and 5B show top and side views of a square aiming assistance fixture 400, which is an alternative embodiment to the circular aiming assistance fixture 300. The areas bounded by references 302 and 404 denote a limit of treatment area. Thus, the circular aiming assistance fixture 300 and the square aiming assistance fixture 400 preferably lie outside of that region. This prevents shots from the excimer laser 20 from actually falling on these fixtures.

The circular aiming assistance fixture 300 and square aiming assistance fixture 400 are attachable fixtures of a known shape which are fixed to the eye within the range of "vision" of the video camera 60 to provide more accurate registration by the eye tracking system 70. These fixtures can be of any other desired shape, of course, and it is simply preferred that they be highly contrasting and of a predetermined profile relative to the remainder of the eye. These fixtures then provide a reliable and easily sensed reference for the eye tracking system 70 to "lock-on" to the origin 102, whether the eye tracking system 70 is light-based, infrared-based, or topographically-based. In an optically-based system, the fixtures are preferably fluorescent. In an infrared system, the fixtures are preferably infrared absorbent, but could be infrared reflecting. In a profile-based system, the fixtures are preferably of a constant height raised profile, as discussed below in conjunction with FIGS. 7 and 8A–8C.

The fixtures are preferably constructed of a lightweight, non-corrosive metal alloy coated with a plastic of the above noted desired properties. They could also be constructed of other lightweight materials, however, such as plastic alone or metal alone. The fixtures should be light enough such that they do not inertially resist movement of the eye 44 and do not appreciably deform the eye 44 during rapid eye movements. That is, the fixtures should be light enough to freely track the movement of the eye 44. For example, they should not be as heavy as the eye retaining rings known in the art and previously used to hold the eye immobile during surgery.

The fixtures can be fixed to the eye through any of a number of means, including suction (such as from a low pressure line and suction ring), friction, using adhesives, or using small "hooks." Such hooks are illustrated on the square aiming assistance fixture 400 as hooks 402. Adhesives should preferably be non-permanent, for example requiring a solvent that is safe to the eye to disolve the bond. Any attachments to the fixture to provide suction should not appreciably resist movements of the eye or deform the eye during such movements. These methods of attachment will be readily apparent to those of ordinary skill in the art.

It will be readily appreciated that other shapes may be used to provide the aiming assistance functionality. For example, a polygonal or star shape could be similarly used. Further, for non-circular ablation patterns, such as for astigmatism, the shape could be oblong, encompassing the treatment area. Finally, the shape need not be completely closed.

Figure 6:
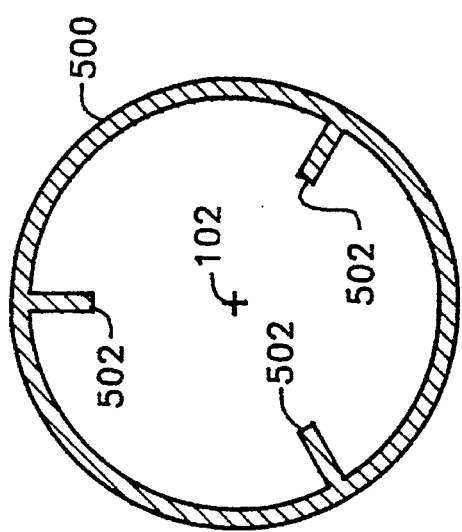
FIG. 6 is a top view of another alternative embodiment of the aiming fixture of FIGS. 4A and 4B.
Figure 8D:
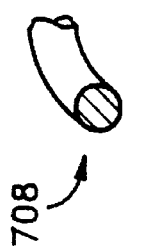
FIGS. 8A–D are cross sectional views of FIG. 7.
Figure 8C:
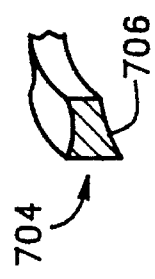
Figure 8B:
Figure 8A:
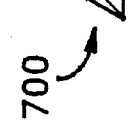

FIG. 6 is a top view of yet another embodiment of an aiming assistance fixture. A circular aiming assistance fixture 500 further includes rotational registration prongs 502. The eye tracking system 70 can further rely upon the rotational registration prongs 502 to compensate for rotational movements of the eye. Other types of rotational registration points will be readily appreciated.

Although in FIGS. 4A, 4B, 5A, 5B, and 6 the origin 102 is shown to be centered within the aiming assistance fixtures, this is for illustrative purposes only. It is not necessary that the aiming assistance fixture be placed with the desired origin 102 exactly centered. When the doctor selects the location of the origin 102, even though it is not centered in the aiming assistance fixture, the eye tracking system 70 will still know the location of the origin 102 relative to the fixture. The fixture provides a fixed and highly observable frame of reference for "locking on" to the origin 102.

Figure 7:
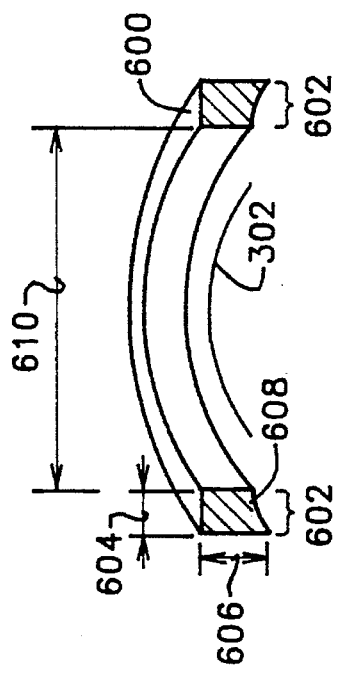
FIG. 7 is a cross sectional view of FIGS. 5A and 5B.

FIG. 7 illustrates a cross sectional view of FIGS. 5A and 5B further defining the circular aiming assistance fixture 300. As can be seen, a wall 600 surrounds the limit of treatment area 302. Specifically, the periphery of the wall 600 forms a substantially closed shape, as seen above in FIGS. 4A and 5A, where the shapes are respectively a circle and a square. The cross sectional view of the wall 600 reveals a profile 602. The profile 602 includes a profile width 604 and a profile height 606. The profile 602 also reveals a base 608, in this embodiment of a curved shape to fit the curvature of the eye. Finally the inner side of the wall 600 has a minimum diameter 610.

The minimum diameter 610 is preferrably larger than treatment area 302. The minimum diameter 610 would in the embodiment of FIG. 5A be the smallest width of the square aiming assistance fixture 400. For example, for a 7.00 mm treatment area 302, the minimum diameter 610 could be, for example 8.00 mm. The minimum diameter 610, however, should not be so great that it lies beyond the range of observation of the eye tracking system 70.

The profile height 606 and profile width 604 are preferrably much smaller than the minimum diameter 610. For example, with the minimum diameter 610 of 8.00 mm, the profile height 606 could be approximately 1.00 mm and the profile width 604 would preferably be approximately 0.50 mm. This small profile 602 serves two-fold purposes. First, the circular aiming assistance fixture 300 is then small enough not to contact the eyelid even when the eye 44 moves. Second, this reduces the overall weight of the circular aiming assistance fixture 300.

The shape of the profile 602 can be varied. By way of examples, FIGS. 8A–8D illustrate alternative profiles to the profile 602. These include a triangular profile 700, a half-torus profile 702, a concave profile 604 with a curved base 706, and a circular profile 708. It will be readily appreciated that numerous other profiles could be chosen without departing from the spirit of the invention. Further, the profile need not be of the same shape around the entire fixture.

It will be appreciated that all of the method and apparatus according to the invention assists an eye tracking system in tracking the eye and the entire surgery system in accurately placing its shots. The aiming assistance fixtures provide a more readily detectable frame of reference, the registration beam provides for precise aiming, and the infrared illumination and filtering provides for improved contrast and immunity to changes in visible light.

The foregoing disclosure and description of the invention are illustrative and explanatory thereof, and various changes in the size, shape, materials, components, circuit elements, wiring connections and contacts, as well as in the details of the illustrated circuitry and construction and method of operation may be made without departing from the spirit of the invention.

What is claimed is:

1. A computer system based method of accurately aiming a pulsed laser beam onto an eye in a system with a low power registration laser beam for providing a laser spot on the eye indicating where a shot of the pulsed laser beam will strike the eye the low power registration laser beam being parallel to the pulsed laser beam;

an aiming system controlled by the computer system for adjusting the aim of the pulsed laser beam and the registration laser beam onto the eye;

a computer system controlled eye tracking device that tracks a fixed point on the eye, that provides central point coordinates of a central point on the eye, and that provides registration coordinates of where the registration laser beam strikes the eye relative to the tracked central point on the eye; and the computer system running ablation profile software for calculating next shot coordinates of where on the eye relative to the central point on the eye a next pulse of the pulsed laser beam should be fired, the method comprising the compute system operated steps of;

calculating the next shot coordinates:

generating an error vector by comparing the registration coordinates of where the low power registration laser beam strikes the eye relative to the tracked central point of the eye to the next shot coordinates of where the next pulse of the pulsed laser beam should be fired relative to the tracked central point of the eye;

adjusting the aim of the pulsed laser beam and the registration laser beam using the aiming system in response to said generated error vector; and firing a pulse of the pulsed laser beam after said adjusting step.

2. The computer system based method of claim 1, wherein the computer system controlled eye tracking device establishes the fixed point on the eye as an origin and provides the central point coordinates and the registration coordinates both normalized to the origin, and wherein said step of calculating the next shot coordinates further comprises the computer system operated step of:

calculating the next shot coordinates normalized to the origin; and wherein said step of generating an error vector further comprises the computer system operated steps of:

normalizing the registration coordinates to the origin; and subtracting the normalized registration coordinates from the normalized next shot coordinates giving the error vector.

3. The computer system based method of claim 1, wherein the computer system controlled eye tracking device establishes the fixed point on the eye as an origin and provides the central point coordinates and the registration coordinates both normalized to the origin, and wherein said step of calculating the next shot coordinates further comprises the computer system operated steps of:

calculating the next shot coordinates normalized to the central point coordinates; and wherein said step of generating an error vector further comprises the computer system operated steps of:

normalizing the registration coordinates to the central point coordinates; and subtracting the normalized registration coordinates from the normalized next shot coordinates giving the error vector.

4. The computer system based method of claim 1 further comprising the computer system operated step of:

repeating said comparing step and said adjusting step until said error vector has a magnitude below a predetermined threshold before performing said firing step.

5. The computer system based method of claim 1, wherein the pulsed laser beam and the registration laser beam are displaced from each other and wherein said comparing step further comprises the computer system operated step of:

adding an offset vector to said error vector, said offset vector corresponding to the displacement of the pulsed laser beam from the registration laser beam.

6. The computer system based method of claim 1, wherein said step of adjusting the aim further comprises the computer system operated step of:

adjusting the aim in an amount directly proportional to said error vector.

7. The computer system based method of claim 1, wherein ambient visible and infrared light strike the eye, wherein the registration laser beam is an infrared beam, and further comprising the computer system operated step of:

filtering non-infrared light such that an infrared image of the eye is created for use by the eye tracking system.

8. The computer system based method of claim 1, wherein the pulsed laser beam is provided by an excimer laser, and wherein said step of firing a pulse further comprises the computer system operated step of:

firing an excimer pulse of the pulsed laser beam.

9. A system for adjusting the aim of a pulsed laser beam onto an eye in response to registration coordinates of a registration aiming laser beam striking the eye, the registration coordinates being provided relative to a fixed point on the eye by an eye tracking system that tracks that fixed point on the eye, the system comprising:

a pulsed laser providing the pulsed laser beam;

a low power registration laser providing the registration laser beam for providing a laser spot on the eye indicating where a shot of the pulsed laser beam will strike the eye, the low power registration laser beam being parallel to the pulsed laser beam;

a computer system based controller including
means for calculating a next desired shot location of where the next pulse of the pulsed laser beam should be fired onto the eye relative to a center location of the eye, and
means for generating an error off set by comparing said next desired shot location of where the next pulse of the pulsed laser beam should be fired with the registration coordinates of where the registration laser beam strikes the eye relative to the fixed point on the eye;

means for aiming the pulsed laser beam and the registration laser beam, said aiming means coupled to said controller and responsive to said error offset; and means for firing a pulse of the pulsed laser beam.

10. The system of claim 9, wherein said means for aiming further comprises:

means for adjusting the aim of the pulsed laser beam and the registration laser beam in direct proportion to said error offset.

11. The system of claim 9, wherein said means for generating an error offset further comprises:

means for adding a misalignment offset to said error offset, said misalignment offset corresponding to a misalignment of the pulsed laser beam and the aiming laser beam.

12. The system of claim 9, wherein the registration laser beam is an infrared beam, wherein ambient visible and infrared light strike the eye, and further comprising:

an infrared filter for filtering non-infrared light such that an infrared image of the eye is created for use by the eye tracking system.

13. The system of claim 9, wherein the pulsed laser is and excimer laser.

* * * * *

UNITED STATES PATENT AND TRADEMARK OFFICE
CERTIFICATE OF CORRECTION

PATENT NO. : 5,620,436
DATED : 04/15/97
INVENTOR(S) : STEFAN LANG and DAVID R. CLONTS It is certified that error appears in the above-identified patent and that said Letters Patent is hereby corrected as shown below:

In column 3:
    line 35, please delete "ophthalmological" and insert in its place ---Ophthalmological---; and
    line 37, please delete "ophthalmic" and insert in its place ---Ophthalmic---.

In column 10:
    line 14, please delete "604" and insert in its place ---704---;
    line 39, please insert ---,--- between "eye" and "the"; and
    line 54, please delete "compute" and insert in its place place ---computer---; and please delete ";" and insert in its place ---:---.

Signed and Sealed this

Eighth Day of July, 1997

Attest:

BRUCE LEHMAN

Attesting Officer

Commissioner of Patents and Trademarks